United States Patent [19]
Bordignon et al.

[11] Patent Number: 5,692,602
[45] Date of Patent: Dec. 2, 1997

[54] PACKAGE FOR SURGICAL SUTURE PROVIDED WITH NEEDLE

[75] Inventors: Marcos Andre Bordignon; Jose Lucio Leite Januzzelli, both of Sao Jose dos Campos, Brazil

[73] Assignee: Ethicon, Inc., Somerville, N.J.

[21] Appl. No.: 594,744

[22] Filed: Jan. 31, 1996

[51] Int. Cl.$^6$ ............... B65D 85/04; B65D 82/24
[52] U.S. Cl. ............ 206/63.3; 206/227; 206/380
[58] Field of Search .................. 206/227, 380, 206/388, 63.3

[56] References Cited

U.S. PATENT DOCUMENTS

| | | | |
|---|---|---|---|
| 4,496,045 | 1/1985 | Ferguson et al. | 206/63.3 |
| 4,555,016 | 11/1985 | Aday et al. | 206/380 |
| 5,101,968 | 4/1992 | Henderson et al. | 206/227 |
| 5,277,299 | 1/1994 | Holzwarth et al. | 206/63.3 |
| 5,344,005 | 9/1994 | Kettner et al. | 206/63.3 |
| 5,427,243 | 6/1995 | Roshdy | 206/63.3 |
| 5,494,154 | 2/1996 | Ainsworth et al. | 206/63.3 |
| 5,529,175 | 6/1996 | Brunken | 206/63.3 |
| 5,533,611 | 7/1996 | Bordighon et al. | 206/63.3 |

*Primary Examiner*—Jimmy G. Foster
*Attorney, Agent, or Firm*—Emil Richard Skula

[57] ABSTRACT

A package for surgical sutures and needles. The package has an elongated retention panel with a needle park and a plurality of openings in the retention panel to receive winding pins for winding a suture onto the retention panel. The package also has a foldably connected second retention panel and first and second ancillary retention panels.

1 Claim, 3 Drawing Sheets

PACKAGE FOR SURGICAL SUTURE PROVIDED WITH NEEDLE

TECHNICAL FIELD

This invention refers to a package or foldable retainer for surgical products, more specifically a package comprising several foldable panels, which is particularly appropriate to retain a sterilized surgical suture made of polymeric material provided with elastic memory, having at least one needle attached thereto.

BACKGROUND OF THE INVENTION

Some types of packages for surgical sutures are already known, which vary in accordance with the nature of the suture and the purpose thereof. In general, the main function of such packaged is that of protecting the suture and respective needle(s) during transportation, handling and storage until it(they) reach(es) the final user. In addition, the most improved start-of-the-art packages have a low manufacturing cost and their structural conception renders opening thereof an easy procedure, allowing the suture-needle set to be quickly reached and removed from the package for use.

The previous technique mostly pertaining to this invention is the one represented by Brazilian patent applications PI 9301757 and PI 9004553, in the name of Johnson & Johnson, which contents are herein incorporated by reference.

The mentioned patent application PI 9301757 is the most relevant for this invention and refers to a foldable package for surgical products, particularly adapted to receive a filamentary surgical product and comprises first and second elongated retention panels, which are foldable united between them through their longitudinal edges, the filamentary surgical product being wound up in a non-inter-crossed manner over the first retention panel; and first ancillary retention panel foldably united to a transversal edge of the first retention panel; and a first elongated locking panel, which longitudinal edge is foldably united to the longitudinal edge of the retention panel, the first locking panel having a substantially transversal weakened line.

The package as per the patent application describing the previous technique also contemplates a tongue-slot-type locking device, the respective slot arranged in a transversely median position in relation to the first retention panel; and ports provided in the referred first retention panel, arranged along substantially semicircular paths, through which pins enabling the winding up of the filamentary surgical product in a non-inter-crossed manner may pass.

Although such construction described in Brazilian patent application PI 9301757 allows a quite satisfactory solution for previously existing problems arising from the "elastic memory" of the suture thread, which after being removed from the package where it was wound up in an "8" shape tended to remain nodulating, making it difficult to use the same, specially when the thread was made of multi or monofilamentary synthetic material, it still presented some difficulties, namely:

a) the need to rip and fold part of the side panel of the package to expose the needle causes seizing of the needle with the aid of a clamp and removing thereof for use at the surgery room to become yet more complicated; and b) the possibility, in some cases, that the suture may wind up in the foam or similar device intended to fix the needle, upon its removal from the package.

Therefore, this invention patent is intended to solve the mentioned problems still found in the previous technique.

DESCRIPTION OF THE INVENTION

Such goal was attained in this invention through the provision of a package for surgical suture provided with a needle, which comprises a first elongated retention panel, provided with needle fixation means and openings intended to receive ancillary pins for suture winding up; at least a second retention panel, in an adjacent position to the referred first retention panel and united to a longitudinal edge thereof by means of a folding line; a first ancillary retention panel united to a transversal edge of the first retention panel by a folding line; a second ancillary retention panel, united to a transversal edge of the first retention panel in opposite position to the transversal edge that unites the first ancillary retention panel to the first retention panel; and a third ancillary retention panel, united through a folding line to the longitudinal edge of the first retention panel in opposite position to the one adjacent to the referred at least one second retention panel, with the third retention panel having means to provide the engagement and removal of the needle and its corresponding suture as from the said needle fixation means of the first retention panel, without need to open the whole package; and the referred means to provide the engagement and removal of the needle and suture, provided in the third retention panel comprising a window provided in the third retention panel, which is overlaid, at least partially, on the said needle fixation means of the first retention panel, when the third retention panel is folded over the first retention panel along the folding line.

According to a preferred although not essential concrete realization of the invention, the referred at least one second retention panel comprises a flap fixed to the said second retention panel by means of a folding line and having a free end which, when said panel is folded along its folding line over the first retention panel, is supported on the edge of the referred needle fixation means, by defining a ramp, making it easier to remove the suture thread from the package through the referred window.

Pursuant to a yet more preferred although not essential concrete realization of the invention, a flap is provided in an adjacent position to the transversal edge of the referred window, which articulates along the folding line with a free edge thereof, turned to inside the referred window, the mentioned flap cooperating with that flap provided in the said at least second retention panel in order to prevent the suture from hitching in the needle fixation means when the needle is removed from the package through the window.

The package in accordance with this invention provides two main advantages in relation to the one described in the mentioned previous technique:

i) The needle can be more easily removed from the package due to the provision of the referred window through which the needle may be accessed. Thus, it is not necessary to open part of the package to have the needle visible and/or accessible; and, in accordance with a preferred realization of the invention.

ii) The possibility of the suture thread being hitched in the needle fixation means, which is usually made of foam, upon removal of the needle through the window, is eliminated thanks to the flap provided in the second retention panel, which flat defines a ramp just beneath the needle fixation means, causing the thread to slide and pass over the fixation means. This effect is yet more improved when the option of providing a flap just beneath the referred window is used, in which case when the window is closed, it cooperates with the firstly mentioned flap, giving more space for the thread to slide to outside the package through the window.

This invention shall be following described in detail, with reference to the annexed drawings.

Detailed description of the closest previous technique for the invention.

BEST MODE FOR CARRYING OUT THE INVENTION

Figure 1:
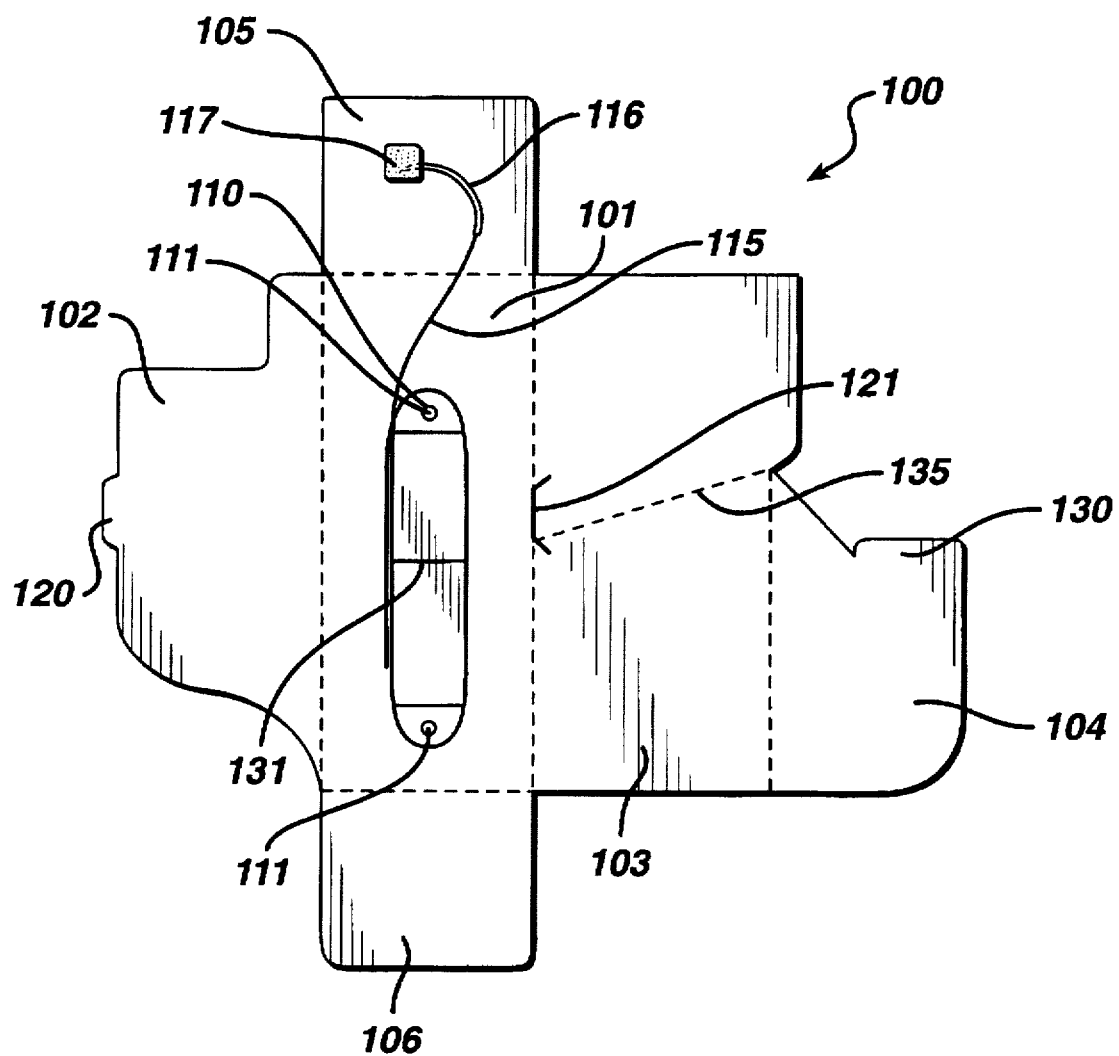
FIG. 1 schematically shows a package for surgical suture provided with needle, pursuant to the description contained in the most pertinent previous technique, in an open position.

As it can be seen in FIG. 1, a package in accordance with the first realization of the previous technique is generically designed by number 100.

Package 100 comprises a first rectangular retention panel 101 and foldably connected through its longer longitudinal edges to a second retention panel 102 and to a first locking panel 103, both also in rectangular shape. This last panel 103 is also connected in a foldable manner, always through its longitudinal edge, to a second locking panel of reduced longitudinal dimensions of the other panels 101 to 103.

Package 100 also includes first and second ancillary retention panels 105 and 106, in approximately square shape, and foldably united to the shorter transversal edges of the first retention panel 101.

In the concrete realization herein described of package 100 as per the previous technique, two ports 110 are provided in the first retention panel 101, through which respective pins 111 are introduced, which have the function of making it easier to manually wind up a suture 115 provided with a needle 116 attached to one of its ends. Optionally, the suture 115 may have a needle 116 fixed to each of its ends, or even not having any needle at all. In addition, package 100 may contain more than one suture 115.

Additionally, suture 115 is wound up in a non-intercrossed manner around pins 111, so that the turns thereof may adopt a substantially oval configuration while they centrifugally expand when they are released.

In the folding of panels 101 to 106 to close and form the definite package 100, the needle 116 is advantageously kept in a separate compartment from the suture 115, thus preventing it to be accidentally cut or the needle 116 edges to be damaged.

The package 100 also includes a first locking device, comprising a first tongue 120, provided in the free longitudinal edge of the second retention panel 102, and a first slot 121, able to harbor the first tongue 120 and arranged in the edge that links the first retention panel 101 to the first locking panel 103. The function of this first locking device 120, 121 is that of keeping the second retention panel 102 folded over the first retention panel 101, with the suture 115 and the second ancillary retention panel 106 between the same.

In an optional concrete realization of such package described in the previous technique, the second ancillary retention panel 106 may be folded over the second retention panel 102, which on its turn is folded over the first retention panel 101 and the suture 115.

A second locking device is also provided, which comprises a second tongue 130, located in the free edge of the second locking panel 104, which axis of symmetry is parallel both to the liking lines between the retention and the locking panels 101–104, and to the longitudinal geometric axis of the package 100 when the same is closed.

Said second locking device also comprises a second slot 131, arranged substantially in the center of the first retention panel 101, between the ports 110, and transversely to the longitudinal geometric axis of said first panel 101.

This second locking device 130, 131 is useful to render the second locking panel 104, immobile over the back face of the first retention panel 101, keeping the package 100 in its folded configuration. Thus, the second locking device 130, 131 causes the existence of the above-mentioned first locking device 120, 121 to be just an optional one.

As shown in FIG. 1, the first locking panel 103 has a weakened line 135 which must be ripped in order that a portion of this first locking panel 103 and, subsequently, the first ancillary retention panel 105 may be raised by a user to obtain access to the suture 115 and to the needle 116.

Figure 2:
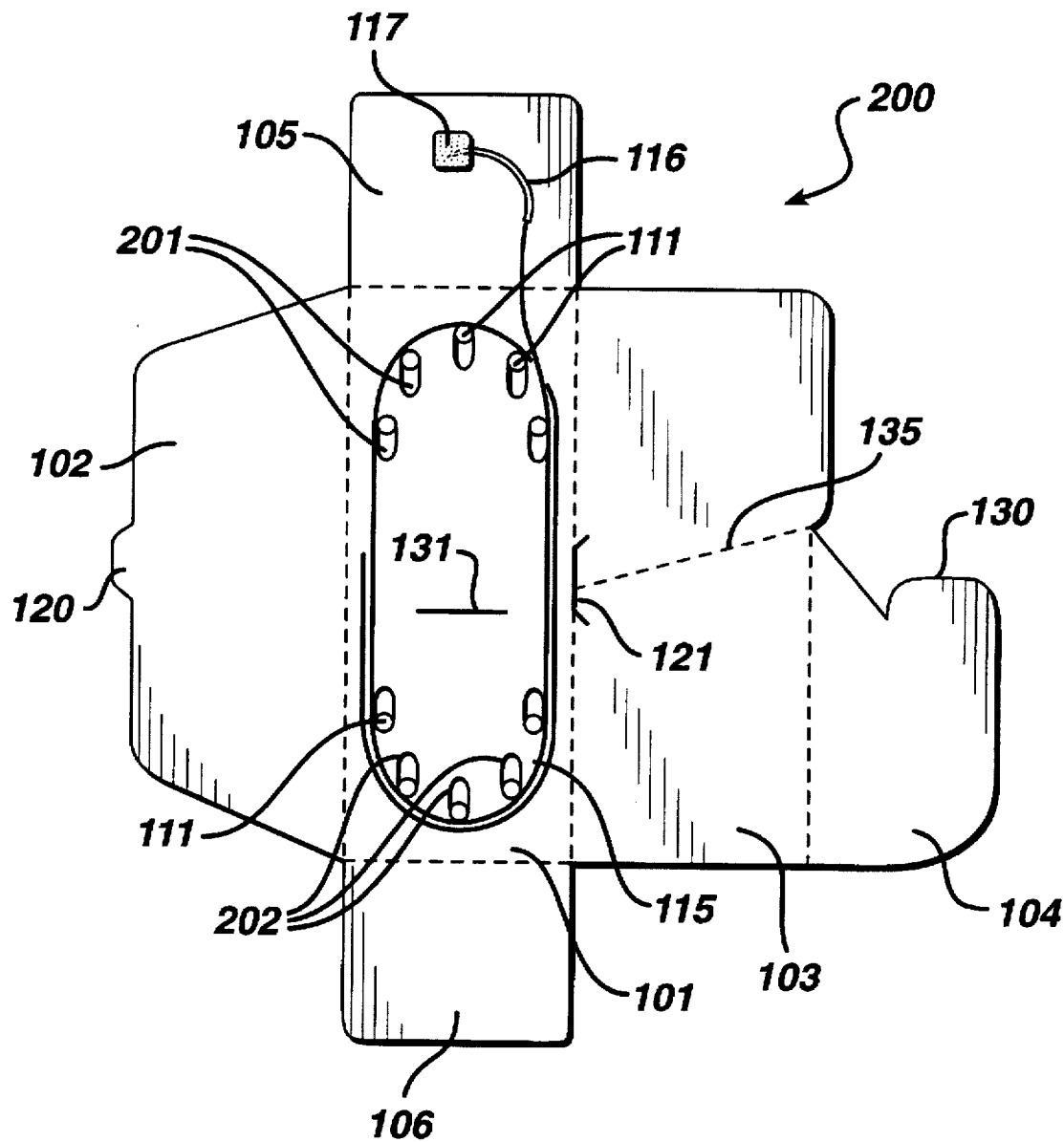
FIG. 2 shows a second concrete realization of the package in accordance with the most pertinent previous technique; and also when it is open.

FIG. 2 refers to a second concrete realization of the closest previous technique of this invention, according to which a package 200 has several portions identical to those comprising the package 100 shown in FIG. 1. Thus, the mentioned portions shall be designed in FIG. 2 with the same reference numbers indicated in FIG. 1.

As it can be seen, the difference between the package 200 and that designated by number 100 in FIG. 1 and above described is restricted to the number and arrangement of ports 201, 202 in the first retention panel 101.

For the package 200 to be able to store surgical sutures provided with any degree of elastic memory with no risk of any portion thereof being unduly retained by the second locking device 130, 131, the turns of the suture 115 must be originally arranged along a substantially circular or oval path. This happens because in those sutures made of materials with lower degrees of elastic memory, such as for example the ones made of material from animal or vegetable origin ("cat gut", silk, cotton, etc.) or woven multifilamentary polymeric material (nylon, polyester, polyethylene, polypropylene, etc.), the trend t centrifugal expansion after winding up may be not enough to assure that the turns of the suture 115 are displaced until reaching the edges of the first retention panel 101, leaving the central portion of said panel 101 entirely free, where the second slot 131 is located.

Thus, in accordance with the concrete realization of the previous technique shown in FIG. 2, said ports 201, 202 are arranged along substantially semicircular paths in respective first and second groups adjacent to the edges of the first retention panel 101, regardless of a centrifugal expansion of the turns of the suture 115.

Description of a Preferred Concrete Realization of the Invention

Figure 3:
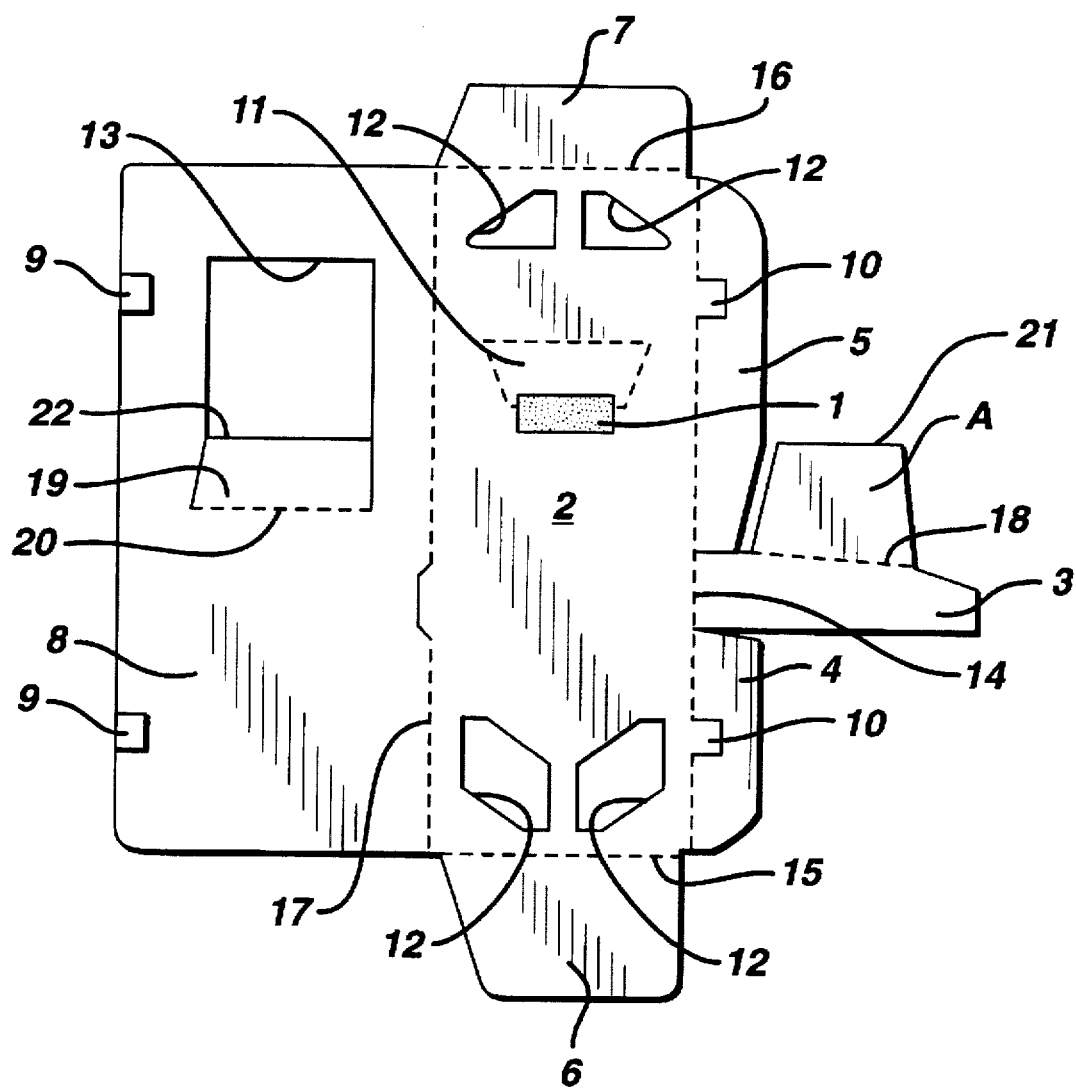
FIG. 3 schematically shows a preferred concreteness of this invention, showing the package in open position.

Reference is herein made particularly to FIG. 3, wherein a package is shown, according to a preferred concrete realization of the invention, which comprises a first elongated retention panel 2, which is provided, approximately in its central region, with a fixation means by way of a foam pad 1, for a needle (not shown) provided in the end of a suture thread (not shown).

A second retention panel formed by three adjacent panel sections 3, 4 and 5 is linked to a longitudinal edge of the first retention panel 2 by a folding line 14. A central section 3 of the referred retention panel 3, 4 and 5 is provided with a flap A, linked thereto through a folding line 18. The function of flap A shall be described in more detail below.

The first retention panel 2 also has, in an adjacent position to its two opposite transversal edges, first 6 and second 7 ancillary retention panels, respectively united to the first retention panel 2 along folding lines 15 and 16. Openings 12 are provided in a conventional form near to the corners of the first retention panel 2, in order to receive pins (not shown) intended to make it easier to wind up the suture thread (not shown) in an "0" configuration, along with edges of the referred first retention panel 2.

A third retention panel 8 is also provided, which is united to the first retention panel 2 by a folding line, along with longitudinal edge of the first panel 2 opposite to the adjacent edge to the second retention panel 3, 4 and 5. The referred third retention panel 8 is also provided with a window 13, the purpose thereof being described in more detail below. The third retention panel is also provided with closing means 9, which cooperate with the corresponding closing means 10 located in the referred first retention panel 2, for closing of the package, as it shall be better explained below.

The package, in accordance with the invention, is assembled as follows: firstly, the foam pad 1 is fixed on the first retention panel 2, after which the needle (not shown) is fixed on the foam pad 1.

The central section 3 of the second retention panel 3, 4 and 5 is folded over the first retention panel 2, in a way to cover part of the foam pad 1 and part of the needle (not shown) which is therein fixed. Following, the suture thread (not shown) provided with the needle is wound up, pursuant to a conventional method, namely, its winding up around pins (not shown) which shall be received in the openings 12. As this stage of winding up of the thread around the pins crossing the openings of said panel 2 is common to the state of the art the same shall not be described in detail.

Following, the two other sections 4 and 5 of the second retention panels 3, 4 and 5 are simultaneously folded over the first retention panel 2. Then, the referred first and second ancillary retention panels 6 and 7 which will also partially cover the referred sections 4 and 5 of the second retention panel 3, 4 and are simultaneously folded over the first retention panel 2.

Finally, the third retention panel 8 is folded over the whole set, thus effecting the interengagement of the cooperating closing means 9 and 10.

Therefore, the needle (not shown) remains visible through window 13, and may be seized and removed through the window 13, without need to open, even though partially, the package.

It must be noted that the window 13 is provided with a flap 19 adjacent to a transversal edge of the window and provided with a free end 21, which flap 19 has the purpose of making it easier to remove the suture thread accompanying the needle, thus cooperating with the flap A provided in the central section 3 of the referred second retention panel 2, in order to prevent the suture thread, upon being pulled by a user, from coiling or being held in the foam pad 1. Thus, while the flap B of the second retention panel 3, 4 and 5 forms a ramp for the thread to slide over it without engaging in the referred foam pad 1, the flap 21, through rising of its free end 21, allows more clearance for the suture thread to pass through the window 13 upon leaving the referred ramp, in order to assure that the thread is not hitched in the pad 1.

It must be noted, however, that the provisions of the referred flap A in the second retention panel 3, 4 and 5 is an optional one and may be eliminated incase the pad made of foam 1 or of any other material may be provided in a trapezoidal and not parallelepipedic form as shown.

It must be then observed that the above described foldable package for surgical products represents a preferred concrete realization of the present invention, the actual scope thereof being defined in the annexed claims.

What is claimed is:

1. A package for surgical suture provided with needle, comprising a first elongated retention panel (2), provided with needle park means (1) for retaining a needle, and openings (12) to receive pins for winding a suture, said panel having a pair of opposed longitudinal edges and a pair of opposed transverse edges;

at least one secondary retention panel (3, 4, 5,) adjacent to the referred first panel (2) and foldably connected to one longitudinal edge thereof along a folding line (14);

a first ancillary retention panel (6) foldably connected to one transverse edge of the first retention panel (2) along a folding line (15);

a second ancillary retention panel (7), foldably connected to the other transverse edge of the first retention panel (2) along a folding line (16);

and a third ancillary retention panel (8), foldably connected along a folding line (17) to the other longitudinal edge of the first retention panel (2);

a first flap (19) adjacent to a transverse edge of a window (13), which can be articulated along a folding line (20) with a free edge (22) thereof, turned to inside of the referred window (13), wherein the flap (19) cooperates with a flap (A) provided in said secondary retention panel (3) in order to prevent a suture from hitching in the needle park means for retaining a needle (1) when a suture is removed from the package through the window (13);

wherein the window (13) in the third retention panel (8), said window having a pair of opposed transverse edges, is overlaid, at least partially, on said needle park means of the first retention panel (2), when the third retention panel (8) is folded over the first retention panel;

wherein the at least one secondary retention panel (3, 4, 5) comprises a second flap (A) foldably connected thereto and having a free end (21) which, when said secondary retention panel (3, 4, 5) is folded over the first retention panel (2), is supported on the edge of the needle park means, defining a ramp over which a suture thread can slide upon being removed from the package, through the window (13).

* * * * *